United States Patent [19]

Dean

[11] Patent Number: 4,629,692
[45] Date of Patent: Dec. 16, 1986

[54] IMMUNOASSAY FOR NONENZYMATICALLY GLUCOSYLATED PROTEINS AND PROTEIN FRAGMENTS AN INDEX OF GLYCEMIA

[75] Inventor: Kenneth J. Dean, Elkhart, Ind.

[73] Assignee: Miles Laboratories, Inc., Elkhart, Ind.

[21] Appl. No.: 446,868

[22] Filed: Dec. 6, 1982

[51] Int. Cl.⁴ .................. G01N 53/00; G01N 33/543
[52] U.S. Cl. ........................................ 435/7; 435/188;
435/810; 436/67; 436/518; 436/811; 436/822;
436/823; 530/322; 530/387
[58] Field of Search ..................... 435/7, 4, 188, 810,
435/291; 436/518, 531, 46, 811, 822, 823, 67,
547, 808, 815, 536; 424/85; 260/112

[56] References Cited

U.S. PATENT DOCUMENTS

| | | | |
|---|---|---|---|
| 4,200,435 | 4/1980 | Stroupe et al. | 23/230 |
| 4,222,836 | 9/1980 | Kerr et al. | 204/180 |
| 4,239,196 | 12/1980 | Acuff et al. | 23/230 |
| 4,247,533 | 1/1981 | Cerami et al. | 424/1 |
| 4,255,385 | 3/1981 | Stroupe et al. | 422/61 |
| 4,268,270 | 5/1981 | Gabbay et al. | 23/230.3 |
| 4,269,605 | 5/1981 | Dean et al. | 23/230 |
| 4,274,978 | 6/1981 | Moore | 252/408 |
| 4,277,560 | 7/1981 | Gray et al. | 435/291 |
| 4,280,816 | 7/1981 | Elahi | 435/7 |
| 4,478,744 | 10/1984 | Mezei et al. | 424/85 |

OTHER PUBLICATIONS

Stevens et al, Proceedings of the National Academy of Science USA., 75: 2918 (1978).
McFarland, Diabetes, vol. 28, Nov. 1979, pp. 1012–1014.
Dolhofer et al, Diabetes, vol. 29, Jun. 1980, pp. 417–421.
Bunn et al, The Journal of Biological Chemistry, vol. 254, No. 10, May 25, 1979, pp. 3892–3898.
Ingelfinger, F. J., New England Journal of Medicine, vol. 296, No. 21, 1977, pp. 1228–1230.

Primary Examiner—Sidney Marantz
Assistant Examiner—William J. Herald
Attorney, Agent, or Firm—Andrew L. Klawitter

[57] ABSTRACT

An immunoassay method and reagent system for determining nonenzymatically glucosylated proteins and protein fragments in a biological fluid based on the specific binding of such proteins and fragments with anti(Amadori-rearranged glucose), e.g., antibodies which selectively recognize the rearranged deoxyfructose form of glucose resulting when proteins are nonenzymatically glucosylated. The antibodies are raised against an immunogen comprising an immunogenic carrier material bearing 1-deoxy-1-fructosyl residues or conformers of such residues. Measurement of nonenzymatically glucosylated proteins and fragments thereof provides a useful index of blood glucose levels.

47 Claims, 2 Drawing Figures

IMMUNOASSAY FOR NONENZYMATICALLY GLUCOSYLATED PROTEINS AND PROTEIN FRAGMENTS AN INDEX OF GLYCEMIA

BACKGROUND OF THE INVENTION

1. Field of the Invention

This invention relates to an immunoassay method and reagent means for determining nonenzymatically glucosylated proteins and protein fragments (e.g., polypeptides, peptides, and amino acids) in a biological fluid such as human serum or plasma. In particular, the present invention concerns a nonradioisotopic, competitive binding, preferably homogeneous, immunoassay method and test kit for such determination. The invention also involves the preparation and use of immunogens which stimulate the production of antibodies which recognize and bind nonenzymatically glucosylated proteins and fragments thereof. The determination of nonenzymatically glucosylated proteins and protein fragments provides a useful index of control of glucose blood levels.

The consequences of diabetes are now known to be much more extensive than simply high extracellular and low intracellular levels of glucose, which can be managed with insulin therapy. A major difficulty in establishing whether there is a relationship between the degree of hyperglycemia and the long-term complications of diabetes has been the lack of a reliable and objective method for assessing diabetic control. Ingelfinger, F. J., *New Engl. J. Med.* 296:1228(1977). It has been found that hemoglobin (Hb) undergoes nonenzymatic glucosylation in vivo (see FIG. 1 of the drawings). Thee first step of nonenzymatic glucosylation involves the formation of an aldimine (Schiff base) between the aldehyde group of glucose and an α- or ε-amino group of a protein. Once formed, the aldimine can either revert back to free glucose and unglucosylated protein or undergo an Amadori rearrangement to a stable ketoamine. This adduct is in equilibrium with its cyclized forms, principally a pyranose ring structure, which are unique to nonenzymatically glucosylated proteins.

The levels of glucosylated Hb (primarily $HbA_{1c}$) have been found to correlate well with the levels of blood glucose that an individual has experienced during the preceding weeks to months (the half-life of Hb in the body is about 60 days) and have been used to monitor the management of blood glucose levels that the diabetic patient has maintained during this time. Reports describing the presence of other nonenzymatically glucosylated proteins in diabetes have appeared: serum albumin [Day, J. F., et al, *J. Biol. Chem.* 254: 595(1979), Dolhofer, R., et al, *Diabetes* 29:417(1980), and McFarland, K. F., at al, *Diabetes* 28:1011(1979)], lens crystallins [Stevens. V. J., et al, *Proc. Natl. Acad. Sci. USA* 75:2918(1978)], lipoproteins [Schleicher, E., et al, *FEBS Letters* 129:1(1981)], collagen [Rosenberg, H., et al, *BBRC* 91:498(1979)], and erythrocyte membrane proteins [Miller, J. A., et al, *J. Clin. Invest.* 65:896(1980)]. In contrast to $HbA_{1c}$ which is characterized by a glucosylated N-terminal valine residue, nonenzymatically glucosylated proteins as a general class are characterized by a multiplicity of Amadori-rearranged glucose residues attached to available amino groups on the proteins (principally ε-amino groups on lysyl residues in the proteins). The extent to which total serum protein is nonenzymatically glucosylated has also been found to correlate well with the mean blood glucose levels maintained by the individual [Bunn, H. F., *Am. J. Med.* 70:325(1981), Kennedy, A. L., et al, *Ann. Int. Med.* 95:56(1981), and Yue, D. K., et al, *Diabetes* 29:296(1980)].

2. Description of the Prior Art

A number of different methods have been developed for the detection of $HbA_{1c}$. Only three of these procedures are being used clinically: (1) cation-exchange chromatography [e.g. SMC® glycosylated hemoglobin (Helena Laboratories) and see U.S. Pat. No. 4,238,196] (2) electrophoresis [e.g. Glytrac® (Corning), see U.S. Pat. No. 4,222,836], and (3) phenylborate affinity chromatography [e.g., Glyco-Gel B, (Pierce Chemical Co.) and see U.S. Pat. No. 4,269,605]. Although these procedures are offered to provide tout speed and convenience, they require isolation of red blood cells preparation of a hemolysate and separation of $HbA_1c$ from Hb prior to detection. In addition, the final separation step in methods (1) and (2) is based on charge differences between Hb and $HbA_1c$ [i.e., glucosylation neutralizes positive charges (α-amino groups) on Hb making the $HbA_{1c}$ more negative relative to Hb]. One consequence of separation by charge is that both the unstable aldimine and the stable ketoamine (see FIG. 1) have the same charge. This can lead to test inaccuracies since the aldimine concentrations will vary widely depending on high transient free glucose concentrations and storage conditions of serum samples.

Certain other methods for determining $HbA_{1c}$ have been described. For example, U.S. Pat. Nos. 4,200,435; 4,255,385 and 4,274,978 concern a spectrophotometric procedure which takes advantage of the spectral changes that occur when 2,3-diphosphoglycerate (2,3-DPG) or inositol hexaphosphate (phytic acid) binds to HbA near the N-terminal amino acid (valine) of the two β-chains. Since the N-terminal valines of the β-chains are glucosylated in $HbA_{1c}$, binding of phytic acid is prevented and no associated spectral changes occur. The change in absorbance induced by phytic acid is, therefore, inversely proportional to the percentage of glycosylated hemoglobin. This technique is limited to the determination of $HbA_{1c}$ since other serum proteins are nonenzymatically glucosylated at amino groups other than the N-terminal amino group (e.g., at lysyl amino groups). Also, it has been reported that the method suffers from interference by fetal hemoglobin (HbF) [Moore, E. G., at al, *Diabetes* 29, Suppl 2:70A(1980)] and endogenous 2,3-DPG [Walinder, O., et al, *Clin. Chem.* 28:96(1982)].

U.S. Pat. No. 4,268,270 describes a method for measuring glycosylated hemoglobin by exposing the sample to oxidizing conditions and measuring the resultant aldehydic compounds.

A radioimmunoassay specific for determining $HbA_{1c}$ is described in U.S. Pat. No. 4,247,533 based on the preparation of an antibody which binds $HbA_{1c}$ with substantially no cross-reactivity for hemoglobins $A_0$, $A_{1a}$ and $A_{1b}$. Such specificity is achieved by administering $HbA_{1c}$ to an animal to stimulate antibody production and screening resulting aniserum for binding to $HbA_{1c}$. The resulting antibody was found to be specific for an antigenic determinant comprising the sugar residue and the adjacent amino acid residues.

An object of the present invention is to provide an antibody selective for binding to Amadori-rearranged glucose residues on glucosylated proteins and protein fragments in general so as to enable the determination of total nonenzymatic glucosylation, principally in relation to serum or plasma proteins. Such determination would be highly selective for nonenzymatic glucosylation because of the selectivity of antibody binding reactions and could be adapted to give a variety of readout signals depending on the immunoassay principle that would be applied. The immunoassay determination of nonenzymatically glucosylated proteins in the blood would provide a very useful index of glycemia.

SUMMARY OF THE INVENTION

The present invention provides an immunoassay method for determining nonenzymatically glucosylated proteins and protein fragments in a biological fluid based on the use of anti(Amadori-rearranged glucose), e.g., antibody which selectively recognizes and binds to Amadori-rearranged glucose residues on glucosylated proteins and fragments thereof. Such anti(Amadori-rearranged glucose) can be prepared in a variety of manners, including conventional antiserum and monoclonal techniques. Principally, antibodies are prepared against an immunogen, preferably synthetically derived, comprising one or more 1-deoxyfructosyl residues, or conformers thereof, covalently linked to an immunogenic carrier. It is preferred to link such haptenic fructosyl residues to or through lysyl residues, e.g., to the ε-amino group on lysyl residues in a carrier protein or polypeptide or through a lysyl linking group to an appropriate carrier material. In one preferred embodiment, such immunogen comprises the haptenic fructosyl residues linked by a bone to amino groups in the carrier and is exemplified by an immunogenic protein or polypeptide such as an albumin or polylysine which has been nonenzymatically glucosylated in vitro.

The immunoassay method can be conveniently practiced in a competitive binding format wherein nonenzymatically glucosylated proteins and fragments thereof in a test sample such as serum, plasma, or urine compete for binding to anti(Amadori-rearranged glucose) with a labeled reagent comprising a detectable label. In a preferred embodiment, a homogeneous immunoassay method is provided wherein the detectable response of the label is altered or modulated by binding of anti(Amadori-rearranged glucose) and the separation step required for immunoassays such as radioimmunoassays is made unnecessary. In such homogeneous assay, the label is preferably a participant in an enzyme-catalyzed reaction, e.g., an enzyme substrate, coenzyme, prosthetic group, or inhibitor, or an enzyme itself.

The present invention also provides appropriate reagent systems, such as in the form of test kits or test devices, for performing the immunoassay method. Also provided are immunogens and their use in preparing antibodies directed against Amadori-rearranged glucose.

DESCRIPTION OF THE PREFERRED EMBODIMENTS

Figure 1:
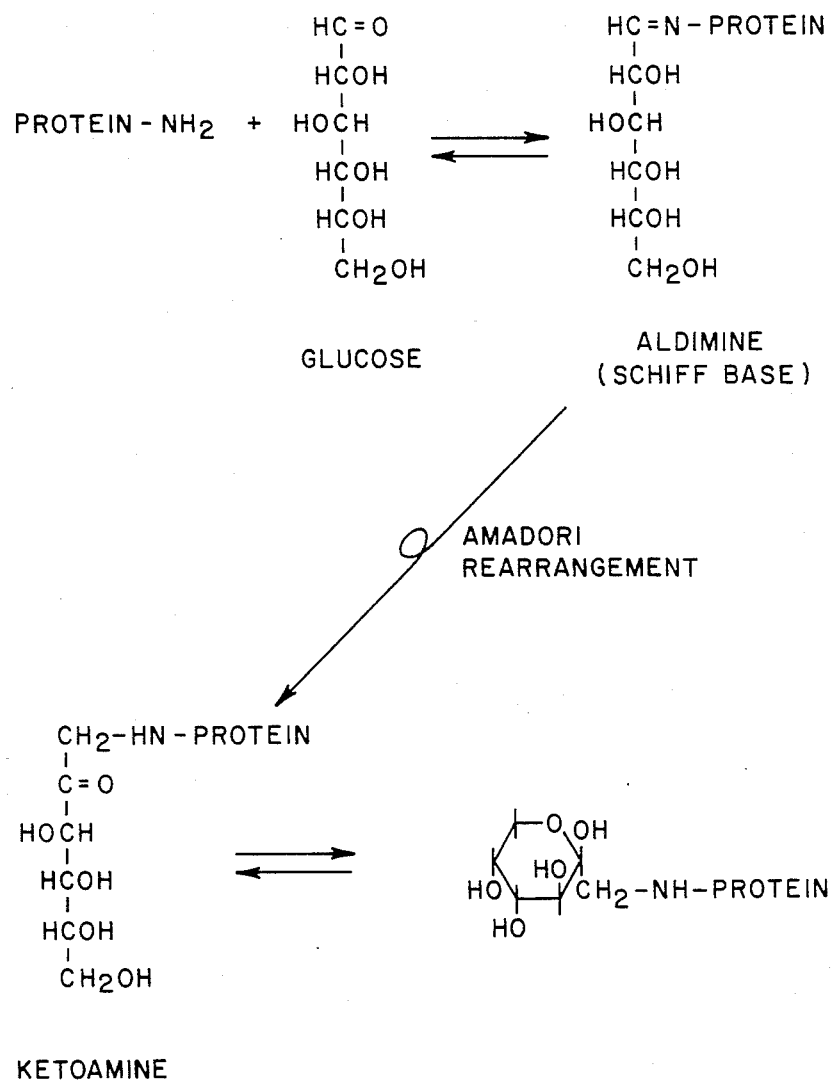
FIG. 1 is a diagram depicting the process of nonenzymatic glucosylation of proteins, including the Amadori-rearrangement step.

At the outset, it is important to understand the usage of certain terminology in this disclosure. As used herein, "Amadori-rearranged glucose" refers to the 1-amino-1-deoxy-D-fructosyl residue, and its conformers, which is the rearranged form taken by glucose upon reaction with amino groups in proteins (see FIG. 1). Such residue has the formula:

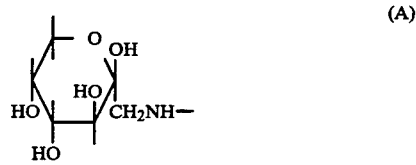

D-fructose is known to exist in several different conformations in solution at equilibrium. This mixture of conformers consists of the open chain ketose, and the α and β anomers of both the six-membered ring D-pyranose and the five-membered ring D-furanose structures. The predominant conformer in the mixture is β-D-fructopyranose [Funcke, W. et al, *Carb. Res.* 50:91976); Parham. P., *TIBS*(July):239(1982); and Angyal, S. J., *Asymmetry in Carbohydrates*, ed. Harmon, R. E., Marcel-Dekker, Inc. (New York 1979) pp. 15–30]. Studies have shown that such conformer also predominates in Amadori-rearranged glucose derivatives of poly-L-lysine [Kraska, B., et al, *J. Carbohydrates, Nucleosides, Nucleotides* 2:241(1975)]. Accordingly, in this disclosure when giving a molecular structure of Amadori-rearranged glucose, the β-D-fructopyranose structure, will be used, i.e., formula (A), with the understanding that the other equilibrium conformers are contemplated as well.

The term "anti(Amadori-rearranged glucose)" as used herein is intended to mean antibodies, and fragments and aggregates thereof as described in detail below, which selectively bind to the Amadori-rearranged glucose residue, formula (A), irrespective of the structure of the haptenic residues on the immunogen used to stimulate production of such antibodies. Various such immunogens will be described in detail below. Accordingly, anti(Amadori-rearranged glucose) is capable of selectively binding to proteins and fragments thereof in a test sample which have been nonenzymatically glucosylated.

"Nonenzymatically glucosylated proteins and fragments thereof" refer to the family of proteins and protein fragments which can appear in a particular biological fluid in a nonenzymatically glucosylated form. Principally, such protein fragments are polypeptides, peptides, and amino acids resulting from the degradation of proteins. In particular, such nonenzymatically glucosylated fragments appear in the urine as degradation products of blood proteins.

ANTI(AMADORI-REARRANGED GLUCOSE)

The anti(Amadori-rearranged glucose) of the present invention can be an antibody, an antibody fragment, or any other substance having a specific binding affinity for Amadori-rearranged glucose and which is derived from immunological processes. When in the form of whole antibody, anti(Amadori-rearranged glucose) can be of any of the known clases, e.g., IgG, IgM, and so forth, and of any subclasses thereof. Any fragment of any such antibody which retains the specific binding affinity for Amadori-rearranged glucose can also be employed, for instance, the fragments of IgG conventionally known as Fab, F(ab'), and F(ab')₂. In addition, aggregates, polymers, conjugates, and chemically modified, e.g., crosslinked, forms of the immunoglobulins or their fragments can be used where appropriate and desirable. Complexes comprising more than one antibody or fragment can be prepared in any available manner so as to maintain the binding affinity for Amadori-rearranged glucose. Likewise, antibodies or fragments thereof can be chemically modified without destroying their anti(Amadori-rearranged glucose) activity such as by intermolecular crosslinking or modification of functional groups for purposes of affecting charge distributions, water or other solvent solubility, temperature stability, and the like as will be known by one working in the field of protein chemistry.

Anti(Amadori-rearranged glucose) immunoglobulins can be obtained by any known means. Numerous texts are available describing the fundamental aspects of inducing antibody formation by conventional antiserum techniques; for example reference may be made to Parker, *Radioimmunoassay of Biologically Active Compounds*, Prentice-Hall (Englewood Cliffs, New Jersey USA, 1976). In the usual case, a host animal such as a rabbit, goat, mouse, guinea pig, or horse is injected at one or more of a variety of sites with an appropriate immunogen, normally in mixture with an adjuvant. Further injections are made at the same site or different sites at regular or irregular intervals thereafter with bleedings being taken to assess antibody titer until it is determined than an acceptable titer has been reached. The host animal is bled to yield a suitable volume of specific antiserum. Where desirable, purification steps may be taken to remove undesired material such as nonspecific antibodies before the antiserum preparation is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, Melchers et al, Springer-Velag (New York 1978), *Nature* 266:495 (1977), *Science* 208:692 (1980), and *Methods in Enzymology* 73(Part B):3-46(1981).

The immunogen used to stimulate production of anti(Amadori-rearranged glucose) immunoglobulins in the most general sense will comprise one or more residues of the formula:

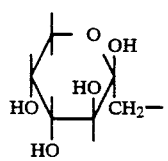

(B)

or conformers thereof, chemically linked, usually by covalent bonds, to an immunogenic carrier material. Such immunogen can be a naturally occurring substance, such as a protein or polypeptide, bearing 1-deoxyfructosyl residues. It is preferred that the immunogen be synthetically prepared by appropriate modification of conventional immunogenic carrier materials used in the preparation of immunogens capable of stimulating production of antibodies which selectively bind a hapten (a small molecule incapable of stimulating antibody production upon injection into the bloodstream of an animal unless conjugated to a macromolecular carrier).

The immunogenic carrier material can be selected from any of those conventionally known having functional groups available for modification with the 1-deoxyfructosyl residue (β). In most cases, the carrier will be a protein or polypeptide, although other materials such as carbohydrates, polysaccharides, lipopolysaccharides, nucleic acids, and the like of sufficient size and immunogenicity can likewise be used. For the most part, immunogenic proteins and polypeptides will have molecular weights between 4,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, and the like. Further reference for the state-of-the-art concerning conventional immunogenic carrier materials and techniques for coupling haptens thereto may be had to the following: Parker, *Radioimmunoassay of Biologically Active Compounds*, Prentice-Hall (Englewood Cliffs, New Jersey USA, 1976); Butler, *J. Immunol. Meth.* 7:1–24(1974); Weinryb and Shroff, *Drug Metab. Rev.* 10:271–283(1974); Broughton and Strong, *Clin. Chem.* 22:726–732(1976); and Playfair et al, *Br. Med. Bull.* 30:24–31(1974).

In a preferred embodiment, the immunogen is synthetically prepared such that the 1-deoxyfructosyl residues (β) are covalently bound to amino groups in the carrier material. In such a case, the carrier material will preferably be an immunogenic protein or polypeptide. Such preferred immunogen has the formula:

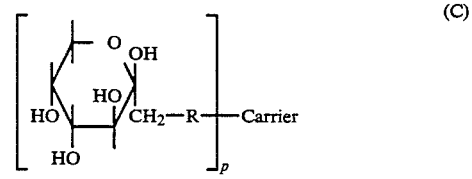

(C)

wherein Carrier is the immunogenic carrier material, p is on the average from 1 to the number of available coupling sites on the carrier material, and R is a bond to an amino group in the carrier. The quantity p in the above formula represents the number of 1-deoxyfructosyl residues that are conjugated to the carrier, i.e., the epitopic density of the immunogen, and will range from 1 to the number of available amino groups on the carrier and can be as high as 5000 in the case of certain high molecular weight synthetic polypeptides such as polylysine. The epitopic density on a particular carrier will depend upon the molecular weight of the carrier and the density of available coupling sites. Optimal epitopic densities, considering the ease and reproducibility of synthesis of the immunogen and antibody response, fall between about 10% and about 50% of the available amino groups on the carrier involved.

In immunogen (C), the haptenic residue will thus have the Amadori-rearranged 1-amino-1-deoxyfructosyl structure of formula (A). One can select any desired polyamine, i.e., a polymer bearing amino groups, and expose it to glucosylating conditions. Such polyamine can be homopolymer or a copolymer. Useful polyamines will be evident in one working in the field and are exemplified by (a) linear poly(amino acids) such as poly-L-lysine, poly-D-lysine, poly-D,L-ornithine, poly-L-ornithine, poly(glutamic acid, lysine) 1:4, poly(lysine, phenylalamine) 1:1, poly(lysine, alanine) 1:1, poly(lysine, tyrosine) 1:1, and poly(lysine, tryptophan) 1:1, (b) branched, multichain poly(amino acids) such as polylysine (polyalanine), polylysine (polyalanine, polytyrosine, glutamic acid), polylysine (polyalanine, polyhistidine, glutamic acid), and polylysine (polyalanine, polyglutamic acid, phenylalanine); (c) polynucleotides such as poly(guanilic acid-5'), poly(cytidylic acid), poly(cytidylic-guanilic acid), poly(deoxyadenylic acid), and poly(deoxyguanilicdeoxy-cytidylic acid), and (d) a variety of other aminobearing polymers or modified polymers, such as polyethyleneimine, poly-L-lysine agarose, lysine Sepharose, aminohexyl Sepharose, and aminosubstituted polyacrylamide [see Schaar, R. L., et al, *J. Biol. Chem.* 253:7949(1978)]. Such polyamines are commercially available from companies such as Miles Laboratories, Inc., Elkhart, IN, U.S. A., Sigma Chemical Co., St. Louis, MO, U.S.A.; and Pharmacia Fine Chemicals, Uppsala, Sweden. It is especially preferred to select polylysine, particularly poly-L-lysine, for glucosylation. Such polylysine, as well as any other selected polyamine, usually will have a molecular weight of between about $10^3$ and about $10^6$ daltons, more commonly between about $10^4$ and $10^6$ daltons.

It is preferred that the carrier be derivatized at lysyl residues, particularly at the $\epsilon$-amino group on lysyl residues in order to mimic the structure of nonenzymatically glucosylated proteins in biological fluids. Polylysine is a preferred carrier for this reason. One can also select a naturally occurring protein or polypeptide and expose it to glucosylating conditions in vitro. This can be readily accomplished by simply exposing an isolated serum protein or protein preparation (e.g., algumin, particularly human serum albumin) to an excess of glucose in aqueous solution. Purified human serum albumin can be obtained by the two-step affinity purification method of Feldhoff and Ledden [*Fed. Proc.* 41:658(1982)]and glucosylation can be performed in vitro as generally described by Dolhofer and Wieland [*FEBS Letters* 103:282(1979)]. The albumin can first be glucosylated and then purified or vice versa.

In vitro glucosylation of a selected naturally occurring or synthetic protein or polypeptide will proceed in buffered solution under mid conditions of pH and temperature and in the presence of excess glucose. Incubation times will usually vary from about 10 to about 20 days without criticality and incubation temperatures from about 35° C. to about 40° C., also without criticality. The reaction can be terminated by common techniques such as ultrafiltration or gel filtration to separate glycosylated material and any unreacted protein or polypeptide from glucose. Unstable aldimine products can be removed by dialysis.

Immunogens of formula (C) can also be prepared where R is an appropriate linking group to the carrier material. Such linking group in general can be of any convenient and stable structure. Such linking group R will usually be in the form of an aliphatic chain comprising between 1 and about 20 atoms, excluding hydrogen, and including heteroatoms such as nitrogen, oxygen, and sulfur. Residue (B) can be joined through a variety of groups to form linking chain R, including methylene, ether, thioether, imino, and the like. One skilled in the art will have a wide variety of linking groups from which to choose to prepare the immunogen. Normally, a 1-deoxyfructosyl derivative will be prepared terminating in a functional group such as amino, carboxyl, thiol, hydroxyl, or maleimido which is active in a coupling reaction to an appropriate group in the carrier molecule. It is most common to form amino or carboxyl derivatives and link them by conventional peptide condensation reactions to counterpart carboxyl and amino groups in the carrier, usually a protein or polypeptide.

A preferred technique for preparing immunogens (C) with a linking group R involves the synthesis of a nonenzymatically glucosylated amino or carboxyl derivative which can then be coupled to the carrier by conventional peptide condensation reactions. Preferably lysine is glucosylated at its $\beta$-amino group such that the resulting immunogen will have a linking group R of the formula:

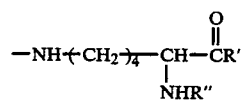

wherein R' is hydroxyl and R" is a bond to a carboxyl group in the carrier, or R" is hydrogen and R' is a bond to an amino group in the carrier. Obvious variations can be made, including the use of lysine analogs, particularly by varying the length of the alkylene chain, or substitution of other groups for hydroxyl and hydrogen for R' and R", respectively, when such are not bonds, e.g., using lower alkyl for R" when not a bond. Other types of amino-functionalized compounds can also be used such as $\omega$-aminoalkanoic acids, e.g., 6-aminohexanoic acid, $\alpha$, $\omega$- diaminoalkanes, e.g., 1,6-diaminohexane, amino-functionalized amino acids, e.g., ornithine and hydroxylysine, as so forth. Techniques resulting in the residue (B) being linked to an amino function are usually preferred since the resulting immunogen will have Amadori-rearranged glucose residues (A). It is particularly preferred that such an amino function be an $\epsilon$-amino group on a lysyl residue, either in the carrier itself or as part of a linking group to the carrier, since the resulting immunogen will more closely mimic glucosylated proteins and their fragments in biological fluids to be assayed.

Highly selective anti(Amadori-rearranged glucose) immunoglobulins can be prepared by monoclonal techniques wherein hybridoma clones are carefully screened for the presence of antibodies which bind to Amadori-rearranged glucose residues. Such screening preferably involves detection of binding of a glucosylated protein, polypeptide, or other appropriate amine different from that used as the immunogen to eliminate antibodies which may bind to antigenic determinants other than Amadori-rearranged glucose. Similarly highly selective antibodies or fragments thereof can be prepared from conventional antiserum preparations by appropriate purification, for example, as described by Good et al, "Purification of Immunoglobulins and Their Fragments", in *Selected Methods in Cellular Immunology*, ed. Mishell and Shiigi, W. H. Freeman and Co. (San Francisco 1980), particularly at pp. 278–281.

IMMUNOASSAY

Anti(Amadori-rearranged glucose) can be used in any immunoassay method for the purpose of determining nonenzymatically glucosylated proteins and their fragments in a biological fluid. Such immunoassay methods include the more classical techniques such as immunodiffusion, immunoelectrophoresis, agglutination techniques, and complement fixation, as well as more current techniques involving the use of specifically detectable labels such as radioimmunoassay and nonradioisotopic methods. The latter techniques can be practiced in a wide variety of formats, however, the present method will usually follow the competitive binding format in which a labeled reagent is made to compete with nonenzymatically glucosylated proteins for binding to anti(Amadori-rearranged glucose). The amount of labeled reagent bound to anti(Amadori-rearranged glucose), or the free-species, consisting of the labeled reagent which is not so bound, is measured appropriately and can be functionally related to the amount of the nonenzymatically glucosylated proteins and fragments in the sample.

In radioimmunoassays, the free-species and bound-species must be physically distinguished or separated in order to measure the label since the signal generated by the label is qualitatively the same in both species. Such a technique is known in the art as heterogeneous because of the phase separation requirement. Other heterogeneous immunoassay techniques are known including enzyme-labeled immunoassays, sometimes referred to as ELISA techniques (see U.S. Pat. No. 3,654,090), and fluorescent immunoassays (see U.S. Pat. Nos. 4,201,763: 4,133,639 and 3,992,631.)

Fairly recently, numerous immunoassay techniques have been developed which obviate the separation step through the use of a label whose detectable signal is modulated upon binding of the labeled reagent by a binding partner, e.g., antibody. Such techniques have become known as homogeneous and are preferred for use in the present invention because separations are not required and radioisotopes are not involved. Some such techniques are fluorescence quenching and enhancement (see U.S. Pat. No. 4,160,016), energy transfer immunoassay (see U.S. Pat. No. 3,996,345), and double antibody steric hinderance immunoassay (see U.S. Pat. Nos. 3,935,974 and 3,998,943). Particularly preferred homogeneous immunoassay techniques are those employing a label which is a participant in an enzyme-catalyzed reaction. Examples are the substrate-labeled immunoassay (see U.S. Pat. No. 4,279,992 and U.K. Pat. Spec. 1,552,607), the prosthetic group-labeled immunoassay (see U.S. Pat. No. 4,238,565), the enzyme modulator-labeled immunoassay, e.g., using inhibitor labels (see U.S. Pat. Nos. 4,134,972 and 4,273,866), and enzyme-labeled immunoassay (see U.S. Pat. No. 3,817,837).

It is particularly preferred to employ anti(Amadori-rearranged glucose) in a homogeneous enzyme substrate-labeled fluorescent immunoassay employing $\beta$-galactosylumbelliferone ($\beta$GU) labels (see U.S. Pat. No. 4,279,992). In order to perform such an assay, a $\beta$GU labeled conjugate is prepared which will compete with nonenzymatically glucosylated proteins and fragments thereof for binding to anti(Amadori-rearranged glucose). For instance, an aminoalkyl derivative of $\beta$GU-carboxylic acid is coupled through a bis-imidate linking arm to amino groups on an appropriate glucosylated protein or polypeptide (e.g., albumin or polylysine). Details of the labeling of proteins and polypeptides in such manner are given in U.S. Pat. No. 4,259,233. The $\beta$GU-labeled conjugate is prepared such that the enzyme $\beta$-galactosidase will cleave the $\beta$-galactosyl group to release an umbelliferone derivative which is highly fluorescent, but if the conjugate is bound by anti (Amadori-rearranged glucose), cleavage is inhibited and fluorescence generation is reduced. In the assay, a test sample of the biological fluid under assay is combined in aqueous solution with $\beta$-galactosidase. The fluorescence read after a given incubation time is a function of the amount of glucosylated protein and fragment in the sample. Standard curves can be generated by performing the assay on reference samples containing known amounts of glucosylated protein and/or fragments thereof.

The reagent system of the present invention comprises all of the essential chemical elements required to conduct a desired immunoassay method encompassed by the present invention. The reagent system or means is presented in a commercially packaged form, as a composition or admixture where the compatibility of the reagents will allow, in a test device configuration, or as a test kit, i.e., a packaged combination of one or more containers holding the necessary reagents. Included in the reagent system are the reagents appropriate for the binding reaction system desired. Of course, the reagent system can include other materials as are known in the art and which may be desirable from a commercial and user standpoint, such as buffers, diluents, standards, and so forth. Particularly preferred is a test kit for the homogeneous competitive binding immunoassay of the present invention comprising anti(Amadori-rearranged glucose) and a labeled reagent capable of binding anti(Amadori-rearranged glucose) and comprising a detectable label, preferably a label which has a property that is altered when bound with the anti(Amadori-rearranged glucose). Also preferred is a test device comprising the reagent composition and a solid carrier member incorporated therewith. The various forms of such test device are described in U.S. patent application Ser. No. 202,378, filed Oct. 30, 1980, which is incorporated herein by reference and which has published as European patent application No. 51,213.

The biological fluid to be assayed according to the present invention will usually be blood or a component thereof, particularly serum or plasma, but may be another appropriate fluid such as urine or saliva. The immunoassay will be allowed to proceed under mild conditions. The reaction mixture will be in general an aqueous medium with any desirable organic cosolvents being present in minor amounts. The temperature of the reaction will be maintained at a constant level in normal circumstances throughout the incubation period and the measurement step. Temperatures will generally be between 5° and 50° C., more usually between 20° and 40° C. Preferably, the reaction will proceed at room temperature. The pH of the reaction mixture will vary between 5 and 10, more usually between 6 and 9. As in the case of the previously described reaction parameters, selection is primarily based on empirically derived optimization balanced against the preferences and needs of the technician who will ultimately perform assays on a routine basis. None of the parameters therefore is of a critical nature to the present invention, rather they are all within the ordinary skill in the art.

The present invention can be applied to the determination of nonenzymatically glucosylated proteins and their fragments in a variety of clinical settings. A principal application is to the assay of blood, e.g., using serum or plasma as the test sample. Individuals with diabetes mellitus have elevated levels of glucosylated proteins in their blood which correlate with their elevated mean blood glucose levels, [Jovanovic, L. and Peterson, C. M., *Am J. Med.* 70:331–338(1981), and Guthrow, C. E., et al, *Proc. Natl. Acad. Sci. U.S.A.* 76:4258–4261(1979)]. When these patients are placed on insulin therapy their mean blood glucose levels immediately drop to near normal levels, however, the elevated levels of glucosylated proteins will persist for a period of time depending on the half-life (lifetime) of the particular protein in blood [Kennedy, L., et al, *Diabetologia* 21:94–89(1981), and Dolhofer, R., et al, *Diabetologia* 21:211–215(1981)]. The persistance of elevated levels of glucosylated proteins in blood provides the physician with an in vivo marker of the diabetic or glucose control that the patient has been able to attain. If the levels of glucosylated proteins remain elevated during the course of insulin therapy, it indicates that the patient is not in good diabetic control and the insulin dosage should be increased.

In contrast, the individuals with hypoglycemia (low blood glucose) have been found to have significantly lower levels of glucosylated protein in their blood compared to normal subjects [Scandellari, C., et al, *Diabetologia* 21:324(1981) and Dolhofer, R., supra]. This condition may arise from insulinoma, for example. Following medical treatment (removal of the tumor in the event of insulinoma) the levels of glucosylated proteins in blood rise to levels indicative of the glucose control that the patient maintains.

The novel antibodies and immunoassay of the present invention can also be applied to the determination of specific nonenzymatically glucosylated proteins or protein fragments or classes thereof by functionally or physically separating or distinguishing such proteins or fragments from other nonenzymatically glucosylated proteins and fragments and measuring the separated glucosylated proteins and fragments. For instance, one can measure any one or any subset of the various types of hemoglobin, e.g., $HbA_1$, by separating such hemoglobin by conventional means from other hemoglobins and/or other proteins in a hemolyzate and applying the present immunoassay to the appropriate fraction. In particular, $HbA_{1c}$ can be separately determined by isolating this hemoglobin fraction such as by phenylborate affinity chromatography and measuring nonenzymatically glucosylated protein, i.e., $HbA_{1c}$, in the fraction using anti(Amadori-rearranged glucose) of the present invention.

Additionally, one can determine nonenzymatically glucoslyated products in urine, such products principally comprising nonenzymatically glucosylated peptides and amino acids which are degradation products of glucosylated blood proteins. In contrast to the testing of urine for sugar level, which is indicative of glucose levels over only a few hours preceding the test, quantitation of nonenzymatically glycosylated amino acids and peptides provides a reflection of the integrated glucose concentration over the period of about one week to one month preceding the test. Accordingly, by quantitating the nonenzymatically glycosylated amino acids and peptides found in urine, it is possible to obtain an accurate reflection of the integrated mean blood glucose concentration. Furthermore, this method is readily adaptable to many clinical environments since it involves only urine sampling. In particular, the method is not only readily useable in the hospital laboratory, but is also readily used for home testing and doctor's office testing.

The present invention will now be illustrated, but is not intended to be limited by the following examples.

Example 1

Preparation of poly[1-deoxy-1-($N^6$-L-lysyl)-D-fructose]

Anhydrous D-glucose [1.4 grams (g), Mallinckrodt Chemical Co., Inc., St. Louis, MO, USA] was added to 50 milliliters (mL) of phosphate-buffered saline (PBS) [10 milligrams (mg) $KH_2PO_4$, 108 mg $NaHPO_4.7H_2O$ and 400 mg NaCl in 50 mL of distilled water containing 100 mg of poly-L-lysine hydrobromide (400,000 daltons mol. wt., Sigma Chemical Co., St. Louis, MO, USA)]. The solution was incubated at 37° C. for 12 days and then it was transferred to dialysis tubing (Spectrum Medical Industries, Inc., Los Angeles, CA., USA) and dialyzed versus 4 changes of 4 (L) liters each of PBS over 5 days. The concentrations of poly-L-lysine and Amadori-rearranged glucosyl residues in the dialyzed solution were determined by the methods of Waddell, W. J., *J. Lab. Clin. Med.* 48:311–314(1956) and Winterhalter, K. H., *Methods Enzymol.* 76:732–739(1981), respectively. The concentration of poly-L-lysine was determined to be 3.3 nanomoles per milliliter (nMol/mL) and the concentration of Amadori-rearranged glucose was 956 nMol/mL, yielding an epitope density of 290 Amadori-rearranged glucosyl residues per poly-L-lysine (Mol/Mol) (15.2% of theoretical).

Example 2

Preparation of Antibodies Selective For Amadori-rearranged Glucose

Rabbits were injected with an immunizing reagent prepared with poly[1-deoxy-1-($N^6$-L-lysyl)-D-fructose] as follows. Poly[1-deoxy-1-($N^6$-L-lysyl)-D-fructose] was diluted to 1 mg/mL with PBS and 5.5 mL of this solution was mixed with 5.5 mL of 0.85% saline and 11.0 mL of Freund's Complete Adjuvant (Miles Laboratories, Inc., Elkhart, IN, USA). Rabbits were injected subcutaneously with 2.0 mL of this emulsion. The rabbits received booster injections of a similar immunizing reagent prepared with Freund's Incomplete Adjuvant (Miles Laboratories, Inc., Elkhart, IN, USA) three weeks after the initial injection and at four-week intervals thereafter.

Serum samples from each rabbit were examined at four-week intervals thereafter by an enzyme-linked immunosorbant assay method as follows.

The antigen used was human serum albumin (HSA) (Miles Laboratories, Inc., Elkhart, IN USA) that had been reacted with glucose by the previously described method [Dolhofer and Wieland, *FEBS Letters* 103:282(1979)] and subsequently purified by dialysis, Affi-Gel Blue chromatography (BioRad Laboratories, Inc., Richmond, CA USA) and Con A-Sepharose chromatography (Pharmacia Fine Chemicals AB, Uppsala, Sweden) by the method of Feldhoff and Ledden [Feldhoff, R. C., and Ledden, D. J., "A Rapid Two-Step Affinity Chromatography Procedure for the Purification of Human and Animal Plasma Albumins", *Fed. Proc.* 41:658(1982)]. A 1 microgram per milliliter ($\mu$g/mL) solution of glucosylated HSA (9.3 Amadori-rearranged glucose residues/HSA, [Mol/Mol]) in 50 (mM) millimoler sodium carbonate buffer, pH 9.6, was prepared and aliquots (100 $\mu$L) were placed in the wells of a microtiter plate (Dynatech Laboratories, Inc., Alexandria, VA, USA). Some wells, to serve as blanks, received only carbonate buffer. After incubating at 37°

C. for three hours, the wells were aspirated and rinsed three times with 200 μL of wash buffer [1 liter of PBS containing 1 g of bovine serum albumin (Miles Laboratories, Inc., Elkhart, IN, USA), 5 mL of Tween 20 detergent (J. T. Baker Chemical Co., Phillipsburg, NJ, USA) and 22.2 g NaCl)]. Aliquots (100 μL) of the serum samples to be examined (diluted in wash buffer) were added to the wells and the plate was incubated at room temperature. After one hour the wells were aspirated and rinsed three times with wash buffer. One hundred μL goat anti-rabbit IgG labeled with peroxidase (Miles Laboratories, Inc., Elkhart, IN, USA), diluted 1:1000 with wash buffer, was added to each well and incubated at room temperature for 45 minutes. Following the incubation the wells were aspirated and rinsed as before. Finally, the wells received 100 μL of peroxidase substrate solution containing 20 μL of 30% hydrogen peroxide, 20 mg o-phenylenediamine (Sigma Chemical Co., St. Louis, MO, USA), 12.0 mL 0.1M citric acid and 5 mL 0.5M Na$_2$HPO$_4$ in 50 mL H$_2$O. After 15 minutes incubation at room temperature the reactions were terminated by the addition of 50 μL 2.5 normal (N) sulfuric acid.

Figure 2:
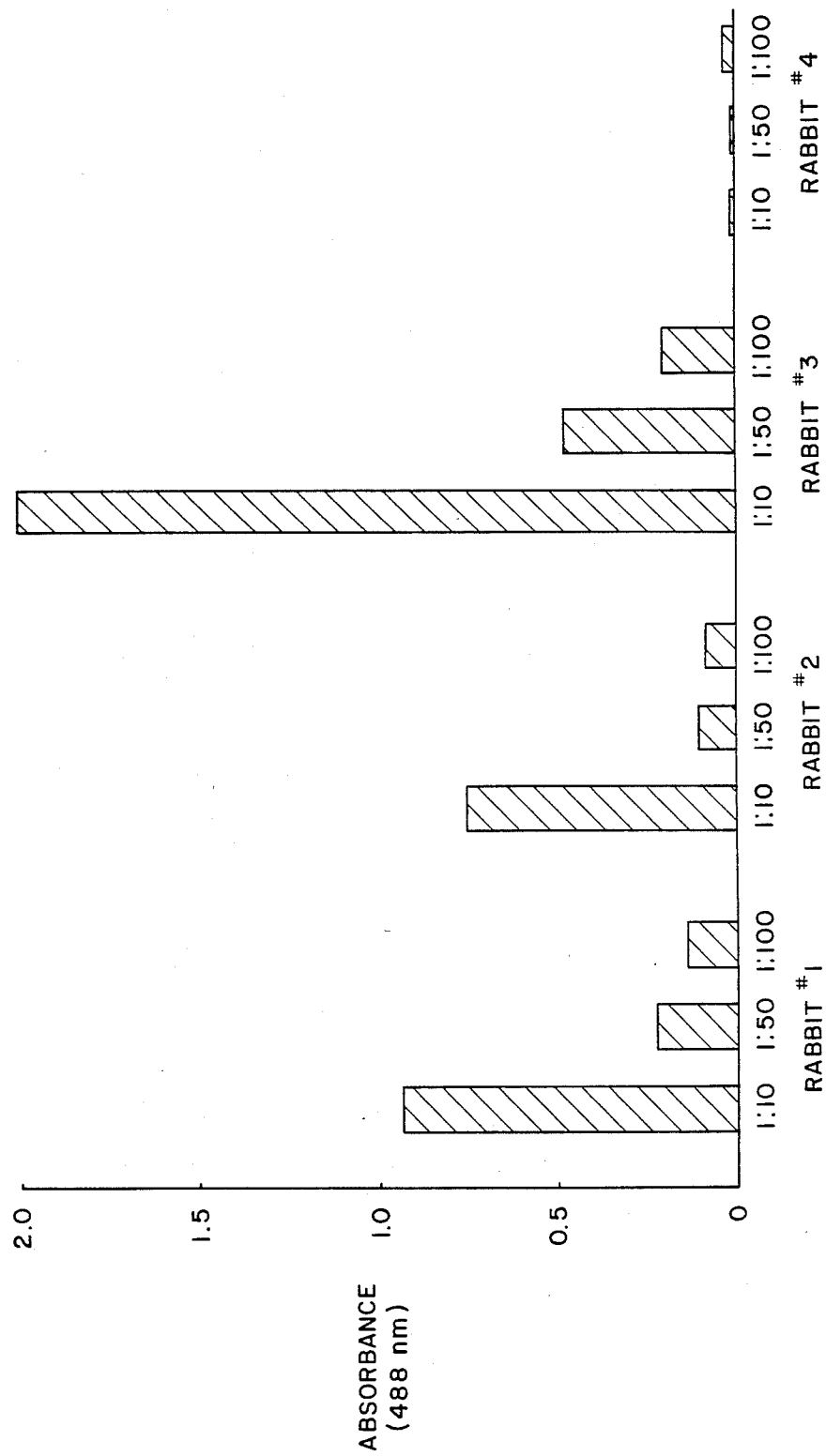
FIG. 2 is a graphical representation of data described in the examples below which demonstrates the preparation of antibodies capable of binding Amadori-rearranged glucose residues, which antibodies were produced against a preferred immunogen of the present invention.

The absorbance of the reaction mixtures was read at 488 nanometers (nm) on an Artek Model 210 Automated Vertical Beam Reader (Artek Systems Corp., Farmingdale, NY USA). These readings for three rabbits responding to the poly[1-deoxy-1-(N$^6$-L-lysyl)-D-fructose] immunogen, and one rabbit that did not (rabbit #4), are shown in Table 1 and FIG. 2.

TABLE 1

| Serum Sample Dilution | | Absorbance at 488 nm |
| --- | --- | --- |
| Rabbit #1: | 1:10 | 0.945 |
| | 1:50 | 0.228 |
| | 1:100 | 0.137 |
| Rabbit #2: | 1:10 | 0.758 |
| | 1:50 | 0.112 |
| | 1:100 | 0.082 |
| Rabbit #3: | 1:10 | 2.002 |
| | 1:50 | 0.483 |
| | 1:100 | 0.207 |
| Rabbit #4: | 1:10 | 0.009 |
| | 1:50 | 0.006 |
| | 1:100 | 0.027 |

The data indicates that the sera from rabbits #1–3 contain antibodies capable of binding to Amadori-rearranged glucose. These serum samples were taken 13 weeks following the initial immunization. All samples taken prior to this time were negative.

Example 3

Preparation of Labeled Reagent

A β-galactosyl-umbelliferone (βGU)-glucosylated human serum albumin reagent can be prepared in the following illustrative manner:

Using the basic method for βGU labeling of proteins as described in U.S. Pat. No. 4,259,233, incorporated herein by reference, N-(6-aminohexyl)-7-β-galactosyl-coumain-3carboxamide in aqueous solution is added to a 2-fold molar excess of dimethyladipimidate dihydrochloride containing a 3-fold molar excess of triethylamine. The reaction mixture is stirred at room temperature for an appropriate period (10 minutes) and the resulting activated reagent added in 10-fold molar excess to glucosylated human serum albumin (Feldhoff and Ledden, supra) in buffer (e.g., 0.1M sodium pyrophosphate, pH 8.5). After the reaction has proceeded for 2 hours at ambient conditions, it is terminated by separating the protein fraction from the other reactants, such as by gel filtration (e.g., Sephadex G-25 from Pharmacia Fine Chemicals). The protein-containing fractions are pooled, dialyzed (e.g., against 0.1M sodium phosphate, pH 7.0, with and without 1M sodium chloride followed by dialysis against 0.1M sodium acetate, pH 5.0), concentrated, such as by ultrafiltration, and stored (frozen at −20° C.).

Example 4

Immunoassay for Amadori-rearranged Glucose

A homogeneous substrate-labeled fluorescent immunoassay (SLFIA-see U.S. Pat. No. 4,279,992) for determining nonenzymatically glucosylated proteins in a biological fluid such as serum can be performed in the following illustrative manner:

A reaction mixture of appropriate volume is prepared to contain an aliquot of the test sample and buffer containing appropriate concentrations of anti(Amadori-rearranged glucose), e.g., antibody as prepared supra, βGU-glucosylated HSA, supra, and the enzyme β-galactosidase. After an appropriate incubation period (e.g., from 1–60 minutes) at room temperature, the fluorescence intensity emitted from the reaction mixture is measured in a fluorometer set for excitation at about 400 nm and emission at about 450 nm. The measured fluorescence is compared to a standard curve relating fluorescence intensity to units of nonenzymatically glucosylated protein. Such a standard curve can be generated by performing the assay protocol on standards in place of the test sample where the standards containing various known levels of glucosylated protein (e.g., glucosylated HSA).

What is claimed is:

1. An antibody which binds specifically to a glucosylated peptide residue comprising Amadori-rearranged glucose and being of the formula:

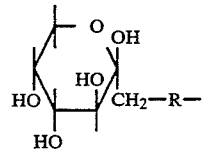

wherein R is a bond, —NH—, or a lysyl residue where the rearranged glucose moiety is coupled to its ε-amino group.

2. The antibody of claim 1 wherein R is a bond.
3. The antibody of claim 1 wherein R is —NH—.
4. The antibody of claim 1 wherein R is said lysyl residue.
5. The antibody of claim 1 prepared against an immunogen comprising one or more residues of the formula:

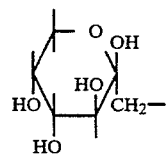

covalently linked to an immunogenic carrier material other than human hemoglobin.

6. The antibody of claim 5 wherein said residue or residues are covalently linked to amino groups in the carrier material.

7. The antibody of claim 6 wherein the amino groups in the carrier material to which said residue or residues are linked are ε-amino groups of lysyl residues.

8. An immunogen for preparing an antibody specific for binding to Amadori-rearranged glucose residues on nonenzymatically glucosylated proteins and fragments thereof, comprising one or more residues of the formula:

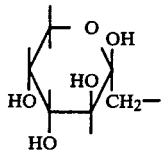

covalently linked to an immunogenic carrier material other than human hemoglobin.

9. The immunogen of claim 8 wherein said residue or residues are covalently linked to amino groups in the carrier material.

10. The immunogen of claim 9 of the formula:

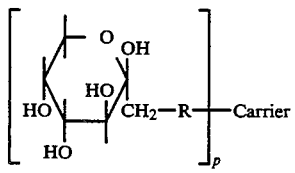

wherein Carrier is an immunogenic carrier material other than human hemoglobin, p is on the average from 1 to the number of available coupling sites on the carrier material, and R is
 (a) a bond to an ε-amino group on a lysyl residue in said carrier material, or
 (b) a linking group of the formula:

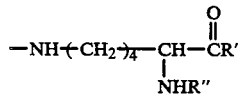

wherein R' is hydroxyl and R" is a bond to a carboxyl group in said carrier material, or R" is hydrogen and R' is a bond to an amino group in said carrier material.

11. The immunogen of claim 10 wherein the carrier material is an immunogenic protein or polypeptide.

12. The immunogen of claim 10 wherein R is said bond and said crrier material is an albumin.

13. The immunogen of claim 10 wherein R is said bond and said carrier material is polylysine.

14. An immunoassay method for determining total nonenzymatically glucosylated proteins and fragments thereof in a biological fluid, comprising the steps of (a) contacting the fluid with an antibody which binds specifically to a glucosylated peptide residue comprising Amadori-rearranged glucose and being of the formula:

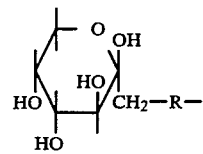

wherein R is a bond, —NH—, or a lysyl residue where the rearranged glucose moiety is coupled to its ε-amino group, and (b) determining binding of proteins and fragments thereof in the fluid to said antibody as a function of the amount of total nonenzymatically glucosylated proteins and fragments thereof in the fluid.

15. The method of claim 14 wherein R is a bond.

16. The method of claim 14 wherein R is —NH—.

17. The method of claim 14 wherein R is said lysyl residue.

18. The method of claim 14 wherein said antibody is prepared against an immunogen comprising one or more residues of the formula:

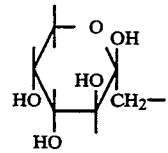

covalently linked to an immunogenic carrier material other than human hemoglobin.

19. The method of claim 18 wherein said residue or residues are covalently linked to amino groups in the carrier material.

20. The method of claim 19 wherein the amino groups in the carrier material to which said residue or residues are linked are ε-amino groups of lysyl residues.

21. The method of claim 14 wherein said fluid is also contacted with a labeled reagent which is capable of binding with said antibody and which comprises a detectable label, and wherein the amount of said label in either the resulting antibody-bound species or the free-species of the labeled reagent is measured as a function of the amount of total nonenzymatically glucosylated proteins and fragments thereof in the fluid.

22. The method of claim 21 of the homogeneous type wherein the label in the labeled reagent provides a detectable response that is different when the ragent is bound to said antibody compared to when not so bound.

23. The method of claim 22 wherein said label is a participant in an enzyme-catalyzed reaction.

24. The method of claim 23 wherein said label is an enzyme substrate, a coenzyme, an enzyme prosthetic group, an enzyme inhibitor, or an enzyme.

25. The method of claim 14 wherein said biological fluid is blood or a component thereof.

26. The method of claim 14 wherein said biological fluid is human serum or plasma.

27. A reagent composition for determining total nonenzymatically glucosylated proteins and fragments thereof in a biological fluid, comprising:
 (1) an antibody which binds specifically to a glucosylated peptide residue comprising Amadori-rearranged glucose and being of the formula:

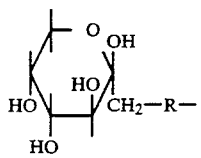

wherein R is a bond, —NH—, or a lysyl residue where the rearranged glucose moiety is coupled to its ε-amino group, and (2) a labeled reagent capable of binding with said antibody and comprising a detectable label.

28. The composition of claim 27 wherein R is a bond.
29. The composition of claim 27 wherein R is —NH—.
30. The composition of claim 27 wherein R is said lysyl residue.
31. The composition of claim 27 wherein said antibody is prepared against an immunogen comprising one or more residues of the formula:

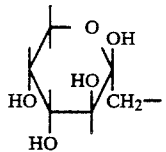

covalently linked to an immunogenic carrier material other than human hemoglobin.

32. The composition of claim 31 wherein said residue or residues are covalently linked to amino groups in the carrier material.
33. The composition of claim 32 wherein the amino groups in the carrier material to which said residue or residues are linked are ε-amino groups of lysyl residues.
34. The composition of claim 27 wherein the label in the labeled reagent provides a detectable response that is different when the reagent is bound to said antibody compared to when not so bound.
35. The composition of claim 34 wherein said label is a participant in an enzyme-catalyzed reaction.
36. The composition of claim 35 wherein said label is an enzyme substrate, a coenzyme, an enzyme prosthetic group, an enzyme inhibitor, or an enzyme.
37. A test device for determining total nonenzymatically glucosylated proteins and fragments thereof in a biological fluid, comprising the reagent composition of claim 27 and a solid carrier member incorporated therewith.

38. A test kit for determining total nonenzymatically glucosylated proteins and fragments thereof in a biological fluid, comprising, in a packaged combination, containers holding:

(1) an antibody which binds specifically to a glucosylated peptide residue comprising Amadori-rearranged glucose and being of the formula:

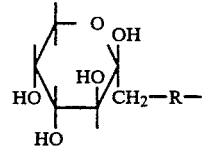

wherein R is a bond, —NH—, or a lysyl residue where the rearranged glucose moiety is coupled to its ε-amino group, and (2) a labeled reagent capable of binding with said antibody and comprising a detectable label.

39. The test kit of claim 38 wherein R is a bond.
40. The test kit of claim 38 wherein R is —NH'.
41. The test kit of claim 38 wherein R is said lysyl residue.
42. The test kit of claim 38 wherein said antibody is prepared against an immunogen comprising one or more residues of the formula:

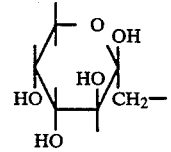

covalently linked to an immunogenic carrier material other than human hemoglobin.

43. The test kit of claim 42 wherein said residue or residues are covalently linked to amino groups in the carrier material.
44. The test kit of claim 43 wherein the amino groups in the carrier material to which said residue or residues are linked are ε-amino groups of lysyl residues.
45. The test kit of claim 38 of the homogeneous type wherein the label in the labeled reagent provides a detectable response that is different when the reagent is bound to said antibody compared to when not so bound.
46. The test kit of claim 45 wherein said label is a participant in an enzyme-catalyzed reaction.
47. The test kit of claim 46 wherein said label is an enzyme substrate, a coenzyme, an enzyme prosthetic group, an enzyme inhibitor, or an enzyme.

* * * * *